(12) United States Patent
Henkes et al.

(10) Patent No.: US 6,207,824 B1
(45) Date of Patent: Mar. 27, 2001

(54) PURIFICATION OF N-SUBSTITUTED LACTAMS

(75) Inventors: Erhard Henkes, Einhausen; Gabriele Iffland; Jürgen Ciprian, both of Ludwigshafen, all of (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/520,172

(22) Filed: Mar. 7, 2000

(30) Foreign Application Priority Data

Mar. 10, 1999 (DE) ............................................. 199 10 504

(51) Int. Cl.[7] ..................... C07D 201/16; C07D 207/04; C07D 211/06; C07D 225/02
(52) U.S. Cl. ................... 540/451; 540/540; 546/290; 548/555
(58) Field of Search ........................... 548/555; 540/451, 540/540; 546/290

(56) References Cited

U.S. PATENT DOCUMENTS

| 3,969,344 | 7/1976 | Ackermann et al. ................ 260/239 |
| 4,831,160 | 5/1989 | Leighton . |
| 5,039,817 | * 8/1991 | Kroker et al. . |
| 5,496,941 | 3/1996 | Ritz et al. ........................... 540/540 |
| 5,777,131 | 7/1998 | Evans . |

FOREIGN PATENT DOCUMENTS

| 35 06 473 | 8/1986 | (DE) . |
| 2 088 850 | 6/1982 | (GB) . |
| 2 325 226 | 11/1998 | (GB) . |
| WO 96/20923 | 7/1996 | (WO) . |

OTHER PUBLICATIONS

Ullmann's Encyclopedia of Industrial Chemisty, 5th Edition vol. A14, (1989) pp. 393–459.

Abrams et al. "A history of the Origin and Development of Macroporous Ion–Exchange Resins" Reactive & Functional Polymers vol. 35 (1997) pp. 7–22.

* cited by examiner

Primary Examiner—Joseph K. McKane
Assistant Examiner—Taofiq A. Solola
(74) Attorney, Agent, or Firm—Keil & Weinkauf

(57) ABSTRACT

A process for reducing the amine content of amine-contaminated N-substituted lactams comprises treating the contaminated N-substituted lactams with an acid macroporous cation exchanger.

11 Claims, No Drawings

PURIFICATION OF N-SUBSTITUTED LACTAMS

The present invention relates to a process for reducing the amine content of amine-contaminated N-substituted lactams.

N-Substituted lactams, for example N-methyl-2-pyrrolidone (NMP), are important as polar aprotic solvents, as synthetic building blocks and as selective extractants, e.g. for the extraction of aromatics from paraffinic hydrocarbons. Particularly for applications in the electronics industry (e.g. lithium ion batteries and photoresist strippers) and in the pharmaceutical industry, there is a need for highly pure N-substituted lactams.

GB-A-2 088 850 discloses a process for treating N-methyl-2-pyrrolidone (NMP) with basic anion exchangers in order to remove acidic or corrosive impurities in the NMP.

U.S. Pat. No. 4,831,160 relates to a process for reducing the concentration of acidic components in NMP in a plurality of steps, where the last step comprises treatment of the NMPs with basic anion exchangers.

DE-A-37 36 603 describes a process for purifying N-vinyl-2-pyrrolidone containing basic impurities of an unknown type by treating the crude N-vinyl-2-pyrrolidone with an acid cation exchanger. Since polymerization of N-vinyl-2-pyrrolidone can occur in the presence of strong acid cation exchangers, weak acid cation exchangers are preferred (—COOH groups as anchor groups).

U.S. Pat. No. 5,777,131 describes a process for improving the properties of N-substituted lactams by treating the lactams after their preparation with ion exchangers, preferably with strong acid cation exchangers of the brands Dowex® G23, Dowex® G26, Dowex® HCR-S and Dowex® HGR.

The Dowex® cation exchangers mentioned are exclusively gel-type styrene-divinylbenzene copolymers functionalized with sulfonic acid groups (—SO$_3$H) as anchor groups (cf. Ullmann's Encyclopedia of Industrial Chemistry, Vol. A14, 5$^{th}$ ed., page 451). The term "gel-type" means that these cation exchangers have a natural porosity with a pore diameter of from about 1 to 3 nm (cf.: Ullmann's Encyclopedia of Industrial Chemistry, Vol. A14, 5$^{th}$ ed., page 395 and pages 399ff, Chapter 3.1 (1989)).

The improvement in the properties of the lactams in accordance with U.S. Pat. No. 5,777,131 constitutes, in the case of NMP, a reduction in the sodium content of about 100 ppb to less than 10 ppb, a reduction in the pH from about 11.5 to 7 and a reduction in the amine content from about 12 ppm to less than 1 ppm.

EP-A-878 454 discloses a process for reducing the content of metallic cations, e.g. alkali metal and alkaline earth metal cations, in organic, virtually water-free liquids such as NMP, isopropyl alcohol, monoethanolamine, dimethylacetamide, ethyl acetate, acetone and sulfolane by bringing the organic liquid into contact with a sulfonated resin based on a styrene-divinylbenzene copolymer in which the proportion of divinylbenzene is from 50 to 60% by weight of the total weight of the copolymer, if the sulfonic acid groups are disregarded.

It is an object of the present invention to find an economical, selective and efficient process for reducing the concentration of amines present as impurities in N-substituted lactams.

We have found that this object is achieved by a process for reducing the amine content of amine-contaminated N-substituted lactams, which comprises treating the contaminated N-substituted lactams with an acid macroporous cation exchanger.

The advantages of the process of the present invention are that these N-substituted lactams which, for example as a result of the method of preparing them, contain amines, e.g. primary amines of the formula RNH$_2$, particularly primary C$_1$–C$_{12}$-alkylamines and C$_1$–C$_4$-monoalkanolamines, such as monomethylamine (MMA), ethylamine, n-propylamine, iso-propylamine, n-butylamine, cyclopentylamine, cyclohexylamine, n-decylamine, n-dodecylamine, monoethanolamine, in particular MMA, as impurities are purified with high selectivity and efficiency.

At the same time, the process of the present invention reduces the concentration of metal cations present in the N-substituted lactams as impurities, e.g. heavy metal ions such as Fe$^{3+}$, Fe$^{2+}$, cd$^{2+}$, Co$^{2+}$, Co$^{3+}$, Cr$^{2+}$, Cr$^{3+}$, Cu$^+$, Cu$^{2+}$, Mn$^{2+}$, Mn$^{3+}$, Ni$^{2+}$, Pb$^{2+}$, Pb$^{4+}$, Sn$^{2+}$, Sn$^{4+}$, Zn$^{2+}$ and Ti$^{4+}$ and alkali metal ions such as K$^+$ and, in particular, Na$^+$ and alkaline earth metal cations, such as Ca$^{2+}$ and Mg$^{2+}$.

The process of the present invention makes possible a high total throughput through the macroporous cation exchanger (unit: [BV]; BV=bed volume=volume of the ion exchanger) and a high hourly throughput through the macroporous cation exchanger (unit: [BV/h]) together with a high capacity of the macroporous cation exchanger (unit: [mol of amine impurity to be removed/liters of ion exchanger]).

Preference is given to using strong acid macroporous cation exchangers, i.e. ones which have –SO$_3$— groups (sulfonic acid groups) as anchor groups.

The acid macroporous cation exchangers are preferably organic macroporous cation exchangers, in particular ones which have a styrene-divinylbenzene copolymer matrix.

In the process of the present invention, the macroporous cation exchangers are used in their acid form (in the H form).

The pore diameter of the macropores in the cation exchangers used in the process of the present invention is generally from 10 to 150 nm and is thus significantly greater than the pore diameter of cation exchangers of the gel type, which have pore diameters of only about 1–3 nm.

The macropores of the cation exchangers used in the process of the present invention preferably have pore diameters of from 20 to 120 nm, particularly preferably from 20 to 100 nm, very particular preferably from 20 to 40 nm.

The significantly larger pores of the cation exchangers used in the process of the present invention result, for example, from the preparation of the styrene-divinylbenzene copolymers being carried out in the presence of nonpolymerizable compounds such as heptane, saturated fatty acids, C$_4$–C$_{10}$-alcohols or polyalcohols or linear polystyrene having a low molecular weight. (Cf.: Ullmann's Encyclopedia of Industrial Chemistry, Vol. A14, 5$^{th}$ Ed., page 395 and pages 399ff, Chapter 3.1 (1989)).

The macroporous cation exchangers used in the process of the present invention generally have a utilizable capacity of at least 0.5 mol, in particular at least 0.8 mol, very particularly preferably at least 1 mol, of amines present as impurities per liter of cation exchanger.

The macroporous cation exchangers used in the process of the present invention can be produced by known methods (cf. Ullmann's Encyclopedia of Industrial Chemistry, Vol. A14, 5$^{th}$ Ed., page 399, last paragraph, and page 400) and are commercially available.

Examples of macroporous cation exchangers in the H form which can be used in the process of the present invention are:

Duolite® C264; Amberlite® 252, UP252 and 200; Imac® C16P; Lewatit® SP112 and K2621; Dowex® 88 and MSC1; Kastel® C300P; Ionac® CFP110; Relite® CFS and CFZ; Diaion® PK 220 and PK 228; Purolite C150, CT165 and CT175; Wofatit® KS10.

Preference is given to using Duolite® C264, Amberlite® 252 and Amberlite® UP252.

The process of the present invention is, in particular, employed for the purification of N-substituted lactams of the formula I

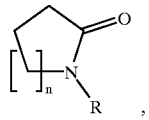

where R is
  a linear or branched saturated aliphatic radical, preferably $C_1$–$C_{12}$-alkyl, such as methyl, ethyl, n-propyl, iso-propyl, n-butyl, iso-butyl, sec-butyl, tert-butyl, n-pentyl, iso-pentyl, sec-pentyl, neo-pentyl, 1,2-dimethylpropyl, n-hexyl, iso-hexyl, sec-hexyl, cyclopentylmethyl, n-heptyl, iso-heptyl, cyclohexylmethyl, n-octyl, 2-ethylhexyl, n-nonyl, iso-nonyl, n-decyl, iso-decyl, n-undecyl, n-dodecyl, iso-dodecyl,
    particularly preferably $C_1$–$C_8$-alkyl such as methyl, ethyl, n-propyl, iso-propyl, n-butyl, iso-butyl, sec-butyl, tert-butyl, n-pentyl and 2-ethylhexyl,
    very particularly preferably $C_1$–$C_4$-alkyl such as methyl, ethyl, n-propyl, iso-propyl, n-butyl, iso-butyl, sec-butyl, tert-butyl, or
  a saturated cycloaliphatic radical having from 3 to 12 carbon atoms, preferably $C_4$–$C_8$-cycloalkyl such as cyclobutyl, cyclopentyl, cyclohexyl, cycloheptyl and cyclooctyl, particularly preferably cyclopentyl and cyclohexyl,
where in these cases the radical R may bear one or two substituents which are inert under the reaction conditions, for example hydroxy or $C_1$–$C_8$-alkoxy (e.g.: R=$C_1$–$C_4$-hydroxyalkyl or $C_1$–$C_8$-alkoxy-substituted $C_1$–$C_4$-alkyl),
and n is an integer from 1 to 4
and where the heterocyclic ring of the N-substituted lactam may bear one or two substituents which are inert under the reaction conditions, e.g. alkyl radicals such as $C_1$–$C_8$-alkyl radicals, which are independent of one another, preferably one $C_1$–$C_8$-alkyl radical.
Suitable substituents on R are, in particular:
hydroxy and
$C_1$–$C_8$-alkoxy such as methoxy, ethoxy, n-propoxy, iso-propoxy, n-butoxy, iso-butoxy, sec-butoxy, tert-butoxy, n-pentoxy, iso-pentoxy, sec-pentoxy, neo-pentoxy, 1,2-dimethylpropoxy, n-hexoxy, iso-hexoxy, sec-hexoxy, n-heptoxy, iso-heptoxy, n-octoxy, iso-octoxy,
  particularly preferably $C_1$–$C_4$-alkoxy such as methoxy, ethoxy, n-propoxy, iso-propoxy, n-butoxy, iso-butoxy, sec-butoxy and tert-butoxy.

Examples of $C_1$–$C_8$-alkyl radicals which the heterocyclic ring of the N-substituted lactam can bear as substituents are:
  methyl, ethyl, n-propyl, iso-propyl, n-butyl, iso-butyl, sec-butyl, tert-butyl, n-pentyl, iso-pentyl and 2-ethylhexyl.

The process of the present invention is particularly preferably employed for the purification of N-substituted lactams of the formula I

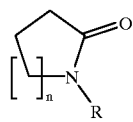

which R is $C_1$–$C_4$-alkyl as described above and may bear a hydroxy substituent and n is 1, 2 or 3.

Examples of N-substituted lactams which can be used in the process of the present invention are: N-methyl-2-pyrrolidone=N-methyl-2-pyrrolidinone=N-methyl-gamma-butyrolactam (NMP), 1,3-dimethyl-2-pyrrolidone, 1,4-dimethyl-2-pyrrolidone, 1,5-dimethyl-2-pyrrolidone, N-ethyl-2-pyrrolidone, N-n-propyl-2-pyrrolidone, N-iso-propyl-2-pyrrolidone, N-n-butyl-2-pyrrolidone, N-iso-butyl-2-pyrrolidone, N-n-pentyl-2-pyrrolidone, N-n-hexyl-2-pyrrolidone, N-cyclohexyl-2-pyrrolidone, N-cyclopentyl-2-pyrrolidone, N-n-decyl-2-pyrrolidone, N-n-dodecyl-2-pyrrolidone, N-benzyl-2-pyrrolidone, N-(2-hydroxyethyl)-2-pyrrolidone, N-(3-hydroxypropyl)-2-pyrrolidone, N-(2-hydroxypropyl)-2-pyrrolidone, N-(2-methoxyethyl)-2-pyrrolidone, N-(1-methoxyethyl)-2-pyrrolidone, N-(2-ethoxyethyl)-2-pyrrolidone, N-methyl-delta-valerolactam, N-(2-hydroxyethyl)-delta-valerolactam, N-methyl-epsilon-caprolactam, N-ethyl-epsilon-caprolactam, N-(2-hydroxyethyl)-epsilon-caprolactam, N-methylheptanoic-omega-lactam, N-(2-hydroxyethyl)-heptanoic-omega-lactam, and also mixtures thereof, preferably NMP and N-(2-hydroxyethyl)-2-pyrrolidone, particularly preferably NMP.

The N-substituted lactams used in the process of the present invention are preferably used in a purity of greater than 90% by weight, in particular greater than 95% by weight, e.g. as distilled product, and can be prepared by known methods, for example by reacting lactones of the formula II

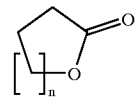

where n is an integer from 1 to 4 and the heterocyclic ring of the lactone may bear one or two substituents which are inert under the reaction conditions, e.g. $C_1$–$C_8$-alkyl radicals which are independent of one another, with amines of the formula $RNH_2$ in which R is as defined above at elevated temperature and superatmospheric pressure with liberation of one mole equivalent of water, e.g. as described in Ullmann's Encyclopedia of Industrial Chemistry, Vol. A22, 5$^{th}$ Ed., page 459 (1993), JP-A-74020 586 (Derwent Abstr. 46186V/25, JP-A-49000 259 (Derwent Abstr.21795V/12), DE-A-19 626 123.

N-Substituted 2-pyrrolidones can also be prepared by reacting maleic anhydride with amines of the formula $RNH_2$ in the presence of hydrogen and a catalyst, e.g. as described in EP-A-745 589.

Examples of lactones of the formula II are:
  gamma-butyrolactone, delta-valerolactone, epsilon-caprolactone, heptanoic omega-lactone, alpha-methyl-gamma-butyrolactone, gamma-valerolactone, gamma-caprolactone, in particular gamma-butyrolactone.

Examples of amines of the formula $RNH_2$ are: monomethylamine (MMA), ethylamine, n-propylamine, iso-propylamine, n-butylamine, cyclopentylamine, cyclohexylamine, n-decylamine, n-dodecylamine and monoethanolamine, in particular MMA.

The process of the present invention can be carried out as follows:

The treatment of the N-substituted lactam with the macroporous cation exchanger for purifying the lactam can be carried out batchwise, for example by stirring the lactam in the presence of the cation exchanger in a vessel, or preferably continuously, for example by passing the lactam through a tube in which the ion exchanger is located as a fixed bed. Suitable examples for methods of operation and tubes containing a fixed bed of ion exchanger may be found, for example, in Ullmann's Encyclopedia of Industrial Chemistry, Vol. A14, $5^{th}$ Ed., pages 431ff, Chapter 10.2 (1989).

In the continuous procedure using a macroporous cation exchanger arranged as a fixed bed in a tube, where the liquid can flow through the ion exchange bed from the bottom upward (upflow mode) or from the top downward, the hourly throughput through the ion exchanger is generally from 0.05 to 100, in particular from 0.1 to 20, very particularly preferably from 0.1 to 10, bed volumes per hour (BV/h) and the empty tube velocity, i.e. the volume flow ($[m^3/h]$) per unit cross-sectional area ($[m^2]$) of the tube, is generally from 0.5 to 40 m/h, in particular from 0.5 to 20 m/h, very particularly preferably from 0.5 to 10 m/h.

The purification process can also be carried out in the presence of inert, polar or nonpolar, protic or aprotic solvents or mixtures thereof which do not react chemically with the cation exchanger, for example water, alcohols such as methanol, ethanol and isopropanol, ethers such as tetrahydrofuran, aromatic or aliphatic hydrocarbons such as toluene, pentane or hexane, or dimethyl sulfoxide (DMSO), a method of operation which is particularly useful when the purified process product is processed further in the form of corresponding solutions.

The temperature is generally in the range from 5 to 130° C., preferably from 10 to 50° C. The process of the present invention is particularly preferably carried out at from 15 to 30° C.

Depending on the type of N-substituted lactam or solution thereof to be purified, the temperature is set at least sufficiently high for the purification process to proceed in the liquid phase.

The regeneration of the cation exchanger used is carried out using known methods and processes according to the cocurrent or countercurrent principle by treatment with an aqueous solution of a Brönsted acid, e.g. by treatment with 4–10% strength by weight, in particular about 7% strength by weight, aqueous hydrogen chloride solution or preferably with 0.5–8% strength by weight, in particular about 5% strength by weight, aqueous sulfuric acid.

Owing to the high throughput (bed volume) possible and the high capacity of the macroporous cation exchangers used in the process of the present invention, these ion exchangers have long operating lives and the intervals between regeneration steps are long. In particular, replacement of the laden cation exchanger by fresh unladen cation exchanger can be more economical than a regeneration step.

Moreover, the process of the present invention has no process-engineering peculiarities, so that further information on this subject is superfluous.

The treatment according to the present invention of the N-substituted lactams, in particular NMP, allows the concentration of amines, in particular amines of the formula $RNH_2$, especially monomethylamine (MMA), which are generally present as impurities in a concentration of up to 10,000 ppm, in particular 1000 ppm, especially 100 ppm, but also in concentrations of greater than 10,000 ppm, to be reduced to concentrations of less than 10 ppm, in particular less than 5 ppm, and this at a throughput through the macroporous cation exchanger of up to 200 bed volumes (BV), in particular up to 500 BV, especially up to 1000 BV (BV based on the solvent-free N-substituted lactam).

At the same time, the treatment according to the present invention of the N-substituted lactams, in particular NMP, allows the concentrations of metal cations such as $Na^+$, $K^+$, $Ca^{2+}$, $Mg^{2+}$, $Fe^{2+}$ and $Fe^{3+}$, in particular $Na^+$, which may be present as impurities in a concentration of generally up to 1000 ppb, in particular 100 ppb, especially 50 ppb, but also in concentrations of greater than 1000 ppb, to be reduced to concentrations of less than 10 ppb, in particular less than 5 ppb, and this at a throughput through the macroporous cation exchanger of up to 200 bed volumes (BV), in particular up to 500 BV, especially up to 1000 BV (BV based on the solvent-free N-substituted lactam).

The ppm and ppb stated are by weight.

EXAMPLES

Comparative Example

N-Methyl-2-pyrrolidone (NMP) having a purity according to GC of 99.8% by area, a sodium ion content of 30 ppb and a monomethylamine (MMA) content of 52 ppm was passed in the upflow mode at 25° C. through a fused silica tube (internal diameter: 30 mm, length: 100 cm) which was filled with the strong acid cation exchanger Dowex® 650 C (Dow Chemical Company) of the gel type in the H form. The bed volume (BV) of ion exchanger was 620 ml. The empty tube velocity was 1 m/h. At a volume flow of 1 BV/h (=hourly throughput), the MMA content of the output from the fused silica tube was more than 5 ppm after only 50 BV had been fed in. After about 120 BV had been fed in, the MMA content was more than 10 ppm and after 170 BV had been fed in it was more than 35 ppm.

After 170 BV had been fed in, the loading of the ion exchanger had reached only 0.22 mol of MMA per liter of ion exchanger.

Example 1

The experiment was carried out as described in the comparative example except that the tube was filled with the strong acid cation exchanger Duolite® C 264 (Rohm and Haas Company) of the macroporous type in the H form. The bed volume (BV) of ion exchanger was 630 ml. The empty tube velocity was 1 m/h. At a volume flow of 1 BV/h (=hourly throughput), the MMA content of the output from the glass tube after 1000 BV had been fed in was still less than 5 ppm.

After 1000 BV had been fed in, the loading of the ion exchanger had reached 1.6 mol of MMA per liter of ion exchanger.

Furthermore, at a volume flow of 1 BV/h, the sodium ion content of the product after 1000 BV had been fed in was likewise still less than 5 ppb.

Example 2

The experiment was carried out as described in the comparative example except that the tube was filled with the strong acid cation exchanger Amberlite® UP 252 (Rohm and Haas Company) of the macroporous type in the H form. The bed volume (BV) of ion exchanger was 630 ml. The empty tube velocity was 1 m/h. At a volume flow of 1 BV/h (=hourly throughput), the MMA content of the output from the fused silica tube after 1000 BV had been fed in was still less than 5 ppm. After 1000 BV had been fed in, the loading of the ion exchanger had reached about 1.4 mol of MMA per liter of ion exchanger. Furthermore, at a volume flow of 1 BV/h, the sodium ion content of the product after 1000 BV had been fed in was likewise still less than 5 ppb.

We claim:

1. A process for reducing the amine content of amine-contaminated N-substituted lactams, which comprises treating the contaminated N-substituted lactams with an acid macroporous cation exchanger.

2. A process as claimed in claim 1, wherein the treatment is carried out using a strong acid macroporous cation exchanger.

3. A process as claimed in claim 1, wherein the cation exchanger has a styrene-divinylbenzene copolymer matrix.

4. A process as claimed in claim 1, wherein the pore diameter of the acid macroporous cation exchanger is from 10 to 150 nm.

5. A process as claimed in claim 1, wherein the utilizable capacity of the acid macroporous cation exchanger is at least 0.5 mol of amine per liter of cation exchanger.

6. A process as claimed in claim 1 for purifying N-substituted lactams of the formula I

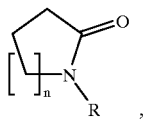

where R is a linear or branched, substituted or unsubstituted, saturated aliphatic or cycloaliphatic radical, n is an integer from 1 to 4 and the heterocyclic ring of the N-substituted lactam has optional inert substituents.

7. A process as claimed in claim 6 for purifying N-substituted lactams of the formula I in which R is $C_{1-4}$-alkyl or hydroxyalkyl and n is 1, 2 or 3.

8. A process as claimed in claim 1 for purifying N-methyl-2-pyrrolidone.

9. A process as claimed in claim 1, wherein the N-substituted lactams are treated with the cation exchanger at from 5 to 130° C.

10. A process as claimed in claim 1, wherein the cation exchanger is employed as a fixed bed.

11. A process as claimed in claim 1, wherein the N-substituted lactams used are ones which have been obtained by reaction of the corresponding lactones with primary amines.

* * * * *